(12) United States Patent
Takagi et al.

(10) Patent No.: US 7,189,415 B2
(45) Date of Patent: *Mar. 13, 2007

(54) RAPIDLY DISINTEGRABLE PHARMACEUTICAL COMPOSITION

(75) Inventors: Hirokazu Takagi, Shizuoka (JP); Atsushi Kajiyama, Shizuoka (JP); Masahiro Yanagisawa, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/998,659

(22) Filed: Nov. 30, 2004

(65) Prior Publication Data

US 2005/0095289 A1 May 5, 2005

Related U.S. Application Data

(63) Continuation of application No. 10/190,568, filed on Jul. 9, 2002, now Pat. No. 6,899,899, which is a continuation of application No. 09/331,235, filed as application No. PCT/JP97/04788 on Dec. 24, 1997, now abandoned.

(30) Foreign Application Priority Data

Dec. 25, 1996 (JP) .............................. P. 8-344768

(51) Int. Cl.
- A61K 9/14 (2006.01)
- A61K 9/20 (2006.01)
- A61K 9/26 (2006.01)
- A61K 9/48 (2006.01)
- A61K 9/66 (2006.01)

(52) U.S. Cl. ............... 424/489; 424/451; 424/455; 424/464; 424/466; 424/469; 424/470

(58) Field of Classification Search ............... 424/489
See application file for complete search history.

(56) References Cited

U.S. PATENT DOCUMENTS

| | | | |
|---|---|---|---|
| 4,404,183 A | 9/1983 | Kawata et al. | |
| 4,673,564 A | 6/1987 | Kawata et al. | |
| 4,946,686 A | 8/1990 | McClelland et al. | |
| 5,091,191 A * | 2/1992 | Oda et al. ................ | 514/399 |
| 5,093,372 A * | 3/1992 | Uedo et al. ................ | 514/687 |
| 5,211,957 A | 5/1993 | Hagemann et al. | |
| 5,399,358 A * | 3/1995 | Baichwal et al. .......... | 424/464 |
| 5,710,150 A * | 1/1998 | Taniguchi et al. ........ | 514/211.15 |
| 5,834,472 A * | 11/1998 | Sangekar et al. ........ | 514/254.07 |
| 6,156,343 A * | 12/2000 | Morita et al. .............. | 424/474 |
| 6,632,455 B2 * | 10/2003 | Sangekar et al. .......... | 424/486 |

FOREIGN PATENT DOCUMENTS

| | | |
|---|---|---|
| EP | 0 051 706 A1 | 5/1982 |
| EP | 0 807 433 A1 | 11/1997 |
| JP | 56-110612 | 9/1981 |
| JP | 59-48810 | 11/1984 |
| JP | 2-704 | 4/1990 |
| JP | 8-127533 A | 5/1996 |
| JP | 08231403 A | 9/1996 |
| JP | 3-240729 | 10/2001 |
| WO | WO 96/19974 | 4/1996 |
| WO | WO 9619974 A1 * | 7/1996 |

OTHER PUBLICATIONS

English translation of Korean Office Action.
S. Radhofer-Welte, P. Dittrich: Determination of the novel non-steroidal anti-inflammatory drug Iornoxicam and its main metabolite in plasma and synovial fluid; Journal of Chromatography B, 707 (1998) pp. 151-159.
Junichi Jinno, et al; Dissolution of Ionizable Water-Insoluble Drugs: The Combined Effect of pH and Surfactant; Journal of Pharmaceutical Sciences, vol. 89, No. 2, Feb. 2000, pp. 268-274.
Burnier, et al, "Pharmacokinetic and pharmacodynamic effects of YMO87, a combined V1/V2 vasopressin receptor antagonist I normal subjects", European Journal of Clinical Pharmacology, vol. 55, p. 633-637, 1999.
Tanaka et al, Book of Abstracts, 211th ACS National Meeting, New Orleans, LA, Mar. 24-28, MEDI-139, American Chemical Society, 1996.

* cited by examiner

Primary Examiner—S. Tran
(74) Attorney, Agent, or Firm—Sughrue Mion, PLLC

(57) ABSTRACT

The present invention relates to a pharmaceutical composition useful for rapid disintegration, which comprises a sparingly soluble medicament held on a gel-forming water-soluble polymer as a solid dispersion, wherein it contains a salt substance that comprises an alkali and a weak or strong acid and has an endothermic standard enthalpy of solution or heat of solution. Since rapid disintegration of the pharmaceutical composition of the present invention and rapid dissolution of the medicament contained in the preparation can be made in the digestive tracts pH-independently, good bioavailability can be attained.

3 Claims, No Drawings

RAPIDLY DISINTEGRABLE PHARMACEUTICAL COMPOSITION

This is a continuation of application Ser. No. 10/190,568, filed Jul. 9, 2002, now U.S. Pat. No. 6,899,899 which is a Continuation of application Ser. No. 09/331,235 filed Jun. 18, 1999, now abandoned which is a National Stage under 35 U.S.C. § 371 of PCT/JP97/04788, filed Dec. 24,1997; the disclosure of which is incorporated herein by reference.

TECHNICAL FIELD

This invention relates to a pharmaceutical composition which comprises a sparingly soluble medicament held on a water soluble polymer as a solid dispersion and exhibits rapid disintegration.

BACKGROUND ART

In order to effect remission and healing of the indication of interest by effectively expressing pharmacological effect of an active ingredient contained in a pharmaceutical preparation, it is needless to say that appropriate dosage form and formulation of the pharmaceutical preparation must be selected depending not only on pharmacological properties of the active ingredient but also on its physicochemical properties and the kind and disease state of the indication of interest.

However, it often occurs that a developed medical compound selected based on its excellent pharmacological effects is sparingly soluble in water despite of the expectation of fast-acting property in its indications.

Since sparingly soluble medicaments are also low in solubility in the digestive tracts, it is general that not only their absorption from the digestive tracts is poor but also their fast-acting property cannot be expected. In addition, in the case of a medicament which becomes sparingly soluble depending on pH, its dissolution property is affected by pH in the digestive tracts and meals of a patient, so that not only its bioavailability after administration is varied but also its fast-acting property cannot be expected in some cases.

In consequence, it is still an important techinical problem to design pharmaceutical preparations to solubilize sparingly soluble medicaments by certain means and to give rapidly disintegrable property, in expectation of attaining fast-acting property of the sparingly soluble medicaments.

Known processes for improving solubility and absorption of a sparingly soluble medicament include a process of finely dividing the medicament, a process for forming a solid dispersion, and the like. Among them, the process for forming a solid dispersion is considered to be generally usable in practice for the improvement of solubility and absorption of a sparingly soluble medicament (cf. an examined Japanese patent publication 59-48810 corresponding to U.S. Pat. No, 4,673,564).

The process for forming a solid dispersion using a polymer base to carry a sparingly soluble medicament is suited for a composition for sustained release preparation. It is however accompanied with the disadvantage that the polymer base formed into a solid dispersion does not contribute to-the disintegration at all so that a disintegrating rate of the preparation in the body liquid is slow, which delays the dissolution of the medicament and therefore fast-acting property cannot be expected.

Also under investigation is a process for improving the absorption of a sparingly soluble medicament hold in a solid dispersion and the disintegration of the preparation. Examples thereof include compression molding obtained by granulating a mixture of a sparingly soluble medicament and a specific polymer such as polyvinyl pyrrolidone by fluidized bed granulation method, and a compression molding obtained by granulating a mixture obtained by compounding a sparingly soluble medicament, one or more components selected from the group consisting of PVP, urea, citric acid, mannitol, succinic acid, methylcellulose, hydroxypropylcellulose, hydroxypropylmethylcellulose and amino acid, and one or more components selected from the group consisting of a surfactant, polyethylene glycol, propylene glycol, glycerol, glycerol fatty acid ester and plant oil by fluidized bed granulation method (cf. an unexamined published Japanese patent application 56-110612). However, there is room for improvement in the above method, particularly, in disintegrable effects. It is desired to establish a formulation technique generally used in practice, for example, by only mixing the components and then compression molding the resultant mixture, without employing the fluidized bed granulation method.

DISCLOSURE OF THE INVENTION

Under such a technical level, the present inventors examined the disintegrable property of the preparation, which was obtained by adding to a composition having a newly developed sparingly soluble medicament held on a polymer base as a solid dispersion, with croscarmellose sodium which was ordinarily used as a general-purpose strong disintegrant, carboxymethylcellulose calcium, starch, low-substituted hydroxypropyl cellulose or the like. As a result, it was found that such a disintegrant could not impart a sufficient disintegrating property to the preparation.

Paying attention to an effervescent preparation composed of sodium bicarbonate and an organic acid such as citric acid or tartaric acid, the present inventors continued investigation. In general, the mixed composition of an alkali and an acid is easily influenced by humidity and therefore it is presumed to involve a problem in the stability. However, it was found unexpectedly that the addition of sodium bicarbonate alone without adding any organic acid makes it possible to impart a rapidly disintegrable property to the preparation and that addition of a specific salt as an alkali which is used for an effervescent preparation also makes it possible to impart a rapidly disintegrable property to the preparation. As a result of further investigation, it was found that a disintegrant used for a preparation having a sparingly soluble medicament held on a polymer base as a solid dispersion can impart the preparation with a desired disintegrable property if it is a salt which comprises an alkali and a weak or strong acid and has an endothermic standard enthalpy of solution or heat of solution, not being limited to sodium bicarbonate. Based on this finding, the present invention was accomplished. The disintegrating mechanism upon the addition of the such a substance has not been made clear yet. However, since the heat of solution when such a substance is dissolved in water is endothermic, the present inventors consider that thermodynamic effects suppress the gelation of a water-soluble polymer and, moreover, the suppression of gelation by salting-out effects of the substance having an endothermic standard enthalpy of solution accelerates the disintegration.

Accordingly, the present invention relates to a rapidly disintegrable pharmaceutical composition which comprises a sparingly soluble medicament held on a gel-forming water-soluble polymer as a solid dispersion, wherein it contains a salt substance that comprises an alkali and a weak or strong acid and has an endothermic standard enthalpy of solution or heat of solution. The present invention also relates to a rapidly disintegrable pharmaceutical composition which comprises a surfactant and a sparingly soluble medicament held on a gel-forming water-soluble polymer as a solid dispersion, wherein it contains a salt substance that comprises an alkali and a weak or strong acid and has an endothermic standard enthalpy of solution or heat of solution. It also relates to a pharmaceutical preparation which comprises 4'-(2-methyl-1,4,5,6-tetrahydroimidazo[4,5-d][l] benzoazepine-6-carbonyl)-2-phenylbenzanilide or a salt thereof and a pharmaceutical carrier that exhibits the dissolution of 75% of said medicament within 15 minutes when a test is performed using 500 ml of the first fluid (pH 1.2) at 100 r.p.m. in accordance with the second method (paddle method) for dissolution specified in *Japanese Pharmacopoeia*, 13th Edition.

It is known to add sodium bicarbonate to a sparingly soluble medicament to improve the dissolution property of the medicament or to add antacid such as sodium bicarbonate to an oxicam-base anti-inflammatory medicament to improve the dissolution and absorption of the medicament (an unexamined published Japanese patent application No. 2-704 corresponding to U.S. Pat. No. 5,091,191, and an unexamined published Japanese patent application No. 3-240729). Such a medicament is not a composition obtained by allowing a large amount of a polymer base to hold the medicament thereon as a solid dispersion, but obtained by using a polymer base upon mixing the medicament with sodium bicarbonate or granulating the resulting mixture.

Hereinafter, the pharmaceutical composition of the present invention is described in more specifically.

With respect to the salt substance which comprises an alkali and a weak or strong acid and has an endothermic standard enthalpy of solution or heat of solution, the term "standard enthalpy of heat" as used herein means a dissolving enthalpy (kJ/mol) at the time when an aqueous solution of standard conditions is produced from 1 mole of a substance under standard conditions.

In addition to the embodiment of the present invention which comprises a salt substance which comprises an alkali and a weak or strong acid, has disintegration improving effects, and has an endothermic standard enthalpy of solution or heat of solution, the present invention embrace an embodiment which further comprises an ordinarily used disintegrant. The present invention also embraces an embodiment within an extent not impairing the object of the present invention, more specifically, the embodiment which further comprises an organic acid such as citric acid within an extent not affecting the pH of digestive tracts.

The sparingly soluble medicament to be used in the present invention is not particularly limited. Its examples include those which show a solubility of 100 ml or more, preferably 1,000 ml or more, more preferably 10,000 ml of more, as the volume of solvent required for dissolving 1 g of each medicament, which is calculated by powdering the medicament, putting the powder into a solvent such as water, the first fluid or the second fluid and then measuring the solubility within 30 minutes when the suspension is vigorously shaken for 30 seconds at 20±5° C. at intervals of 5 minutes. The first fluid and second fluid as used herein are specified in the disintegration test of *Japanese Pharmacopoeia*, 13th Edition. For example, the first fluid is an aqueous solution having a pH value of about 1.2 prepared by filling up 2 g of sodium chloride and 7.0 ml of hydrochloric acid to 1,000 ml with water, and the second fluid is an aqueous solution having a pH value of about 6.8 prepared by filling up 250 ml of 0.2 M potassium dihydrogenphosphate aqueous solution and 118 ml of 0.2 N sodium hydroxide aqueous solution to 1,000 ml with water. Examples of the sparingly soluble medicament include central nervous system drugs, circulatory organ system drugs, respiratory organ system drugs, digestive organ system drugs, antibiotics, chemotherapeutic agents, metabolic system drugs and vitamin drugs, all of which being sparingly soluble. A medicament which requires fast-acting property can be cited as a preferred example of the sparingly soluble medicament to be used in the present invention. Its illustrative examples include 4'-(2-methyl-1,4,5,6-tetrahydroimidazo[4,5-d][l] benzoazepine-6-carbonyl)-2-phenylbenzanilide or a salt thereof which is a known compound disclosed in International Publication 95/03305 (to be referred simply to as "Compound A" hereinafter in some cases, and its hydrochloride as "Compound Al"), (Z)-4'-[[4,4-difluoro-5-[(4-dimethylaminopiperidino)carbonyl]methylene]-2,3,4,5-tetrahydro-1H-1-benzoazepin-1-yl]carbonyl]-2-phenylbenzanilide or a salt thereof which is a known compound disclosed in International Publication 95/06035 and 1-[2,3-dihydro-1-(O-methylphenacyl)-2-oxo-5-phenyl-1H-1,4-benzoazepin-3-yl]-3-(m-tolyl)urea which is a known compound disclosed in International Publication 92/11246 (to be referred to as "Compound B" hereinafter in some cases), of which Compound A is preferred, and Compound Al is more preferred.

The Compound A is created by the inventors in the company of the present applicant, which has excellent antagonism for arginine vasopressin V1 and/or V2 receptor. Based on the profile of this function, it shows water diuretic action, urea excretion enhancing action, factor VIII secretion inhibition action, vasodilation action, cardiac function acceleration action, mesangial cell contraction action, mesangial cell growth inhibition action, hepatic gluconeogenesis action, platelet agglutination inhibition action, aldosterone secretion inhibition action, endothelin production inhibition action, central buffer controlling action, renin secretion controlling action, memory controlling action, body temperature controlling action and prostaglandin production controlling action, is useful as characteristic water diuretic agent, urea excretion enhancing agent, vasodilator drug, hypotensive drug, anti-cardiac failure agent, anti-renal failure agent and blood coagulation inhibitor and is effective in preventing and/or treating diseases such as cardiac failure, hyponatremia, syndrome of inappropriate secretion of antidiuretic hormone (SIADH), hypertension, renal insufficiency, (nephrosis, glomerular nephritis, diabetic naphropathy, chronic or acute renal failure), edema, brain edema, ascites, hepatic cirrhosis, hypokalemia, water metabolism disorder, diabetes, various ischemic diseases, cerebrovascular accidents, circulatory failure, gastric ulcer, nausea, emesis, syncope and renal function disorder and also in alleviating secondary diseases of cerebral infarction and cerebral bleeding.

Since said compound is sparingly soluble in water, it becomes an important technical problem to solubilize Compound A upon designing of its preparation, thereby attaining good bioavailability. In addition, since this compound is expected to increase urine volume due to its pharmacological effects, rapid expression of drug efficacy after administration after supper is desired in order to prevent the expression of drug efficacy while sleeping. It is therefore an important technical problem to impart both rapid disintegration and rapid dissolution properties to a pharmaceutical preparation containing Compound A upon designing of the preparation.

For exhibiting a fast-acting property of Compound A used in the present invention, it is necessary for the pharmaceutical preparation to disintegrate rapidly, thereby rapidly dissolving the medicament contained in the preparation. An example for its evaluation standards is as follows. When a pharmaceutical preparation (e.g., in the form of a tablet) containing Compound A is subjected to a test by using 500 ml of the first fluid (pH: 1.2) at 100 r.p.m. in accordance with the second method (paddle method) of the dissolution test method specified in *Japanese Pharmacopoeia*, 13th Edition, a time required for the dissolution of 75% of Compound A is within 15 minutes. Preferably, a time required for the dissolution of 75% of Compound A is within 10 minutes. The carrier for the preparation is not particularly limited as long as it shows such dissolution behavior. The amount of Compound A is not particularly limited as long as it is a pharmacological amount ordinarily used for the treatment.

The gel-forming water-soluble polymer usable in the present invention is not particularly limited as long as Compound A can generally be held on it as a solid dispersion. Preferred are cellulose derivatives. Specific examples of the cellulose derivative include hydroxypropylmethylcellulose (for example, "TC-5E", "Metolose 90", "Metolose 65SH", each trade name; produced by Shin-Etsu Chemical Co., Ltd.), hydroxypropylcellulose (for example, "Nisso HPC", trade name; produced by Nippon Soda Co., Ltd.), methyl cellulose (for example, "Metolose SM", trade name; produced by Shin-Etsu Chemical Co., Ltd.), and hydroxyethylcellulose ("NATROSOL", trade name; produced by Hercules Japan, Ltd.). More preferred is hydroxypropylmethylcellulose. These gel-forming water-soluble polymers can be used either singly or in combination.

In order to increase the solubility of the solid dispersion of the present invention, a surfactant may be added. The surfactant is not particularly limited as long as it is pharmaceutically acceptable. Examples thereof include anionic surfactants such as sodium alkylsulfate and nonionic surfactants such as polyoxyethylene sorbitan fatty acid esters (for example, Polysorbate 80; "Rheodol TW-0120", trade name; produced by Kao Corp.), polyoxyethylene fatty acid esters and polyoxyethylene castor oil derivatives (for example, polyoxyethylene hydrogenated castor oil (60); "HCO-60", trade name; produced by Nikko Chemicals Co., Ltd.). These surfactants may be used either singly or in combination.

When a solid dispersion of a sparingly soluble medicament and a gel-forming water-soluble polymer or a solid dispersion of a sparingly soluble medicament, a gel-forming water-soluble polymer and a surfactant, each to be used in the present invention, is prepared, the gel-forming water-soluble polymer is added in an amount of 0.5 to 20 parts by weight, preferably 1 to 10 parts by-weight, more preferably 1 to 5 parts by weight, based on 1 part by weight of the sparingly soluble medicament. The surfactant is added in an amount of 0.1 to 3 parts by weight, preferably 0.2 to 1.5 parts by weight, more preferably 0.25 to 1.25 parts by weight based on 1 part by weight of the sparingly soluble medicament.

Examples of the salt substance used in the present invention, which comprises an alkali and a weak or strong acid and has an endothermic standard enthalpy of solution or heat of solution (which may hereinafter be abbreviated as "disintegrable improver", simply) include sodium bicarbonate (19.1 kJ/mol, 4.3 kcal/mol), potassium bicarbonate (5.3 kcal/mol), potassium sulfate (23.7 kJ/mol, 6.38 kcal/mol), potassium chloride (17.2 kJ/mol, 4.19 kcal/mol), sodium chloride (3.9 kJ/mol, 1.18 kcal/mol) and potassium dihydrogenphosphate (19.6 kJ/mol, 4.85 kcal/mol). Among them, preferred are sodium bicarbonate, potassium bicarbonate, potassium sulfate and potassium dihydrogenphosphate. Sodium bicarbonate and/or potassium bicarbonate are more preferred, and sodium bicarbonate is still more preferred. These disintegrable improvers may be used either singly or in combination.

The amount of the disintegrable improver used in the present invention is not particularly limited as long as it is a pharmaceutically acceptable amount. It is preferably added in an amount of at least 0.1 part by weight, more preferably 0.1 to 6 parts by weight, still more preferably 0.3 to 1 part by weight based on 1 part by weight of the gel-forming water-soluble polymer. Amounts smaller than 0.1 part by weight show small effects, and it is desired to suppress the amount of an excipient upon formulation.

The sparingly soluble medicament, gel-forming water-soluble polymer, surfactant and disintegrable improver are added in amounts (wt./wt. %) of 1 to 30%, 3 to 60%, 0 to 20% and 3 to 50%, respectively, preferably 3 to 15%, 10 to 50%, 0 to 10% and 5 to 30%, respectively, each based on the total amount of the preparation.

A preferred pharmaceutical composition or pharmaceutical preparation according to the present invention is that comprising hydroxypropylmethylcellulose as the gel-forming water-soluble polymer, sodium bicarbonate as a salt substance which comprises an alkali and a weak-or strong acid and has an endothermic standard enthalpy of solution or heat of solution, and optional a polyoxyethylene sorbitan fatty acid ester as a surfactant.

Hereinafter, the pharmaceutical composition or the manufacturing process for the preparation of the preparation comprising the same according to the present invention will be described in detail.

A composition which comprises a sparingly soluble medicament held on a gel-forming water-soluble polymer as a solid dispersion and a solid dispersion which comprises a sparingly soluble medicament held on a gel-forming water-soluble polymer containing a surfactant can be prepared in a known manner. For example, a sparingly soluble medicament, a surfactant, etc. can be prepared by suspending or dissolving Compound A and a gel-forming water-soluble polymer and an optional surfactant in water or an organic solvent (e.g., a lower alcohol such as methanol or ethanol, or a halogen-based organic solvent such as dichloromethane) and then spray drying the solution or suspension. Alternatively, the solid dispersion may be prepared by the step of spraying the solution or suspension to an excipient, and then granulating. The granulation can be carried out in a known manner, for example, by a fluidized bed granulator (manufactured by Okawara Seisakujo), a vertical mixer (manufactured by San-Ei Seisakujo) or an agitating granulator (manufactured by Fukae Kogyo). In the case of a fluidized bed granulator, granulation is carried out by generally operable conditions, for example, at a spray pressure of 0.3 to 3 kg/cm$^2$ and product temperature of 20 to 45° C. until the granule size reaches the desired level.

The pharmaceutical preparation of the present invention can be used in the form of tablets, granules or capsules. Among them, compression-molded tablets and capsules having a solid dispersion filled therein exhibit more desirable effects of the present invention. Preparations in such forms can be prepared in a known manner. For example, tablets can be prepared on a single punch tabletting machine (manufactured by Kikusui Seisakujo) or rotary tabletting machine (manufactured by Hata Seisakujo). The molding pressure upon tabletting may be set as desired based on the hardness, disintegrable property, etc. of the molded product and is not particularly limited. Examples of the molding pressure include 0.3 ton/punch to 1 ton/punch.

Such a pharmaceutical preparation can be prepared in a known manner by using, for example, as an additive, an excipient such as lactose, corn starch, light anhydrous silicic acid, microcrystalline cellulose or crystalline cellulose ("Avicel PH102", trade name; product of Asahi Kasei); a binder such as a starch, methylcellulose, carboxymethylcellulose, hydroxypropylcellulose, hydroxypropylmethylcellulose, polyvinyl pyrrolidone, gum arabic powder, gelatin or pullulan; a disintegrant such as croscarmellose sodium ("Ac-Di-Sol", trade name; produced by Asahi Kasei), carboxymethylcellulose calcium, starch or low-substituted hydroxypropylcellulose; a surfactant such as "Polysorbate 80" (produced by Kao Astra Co., Ltd.), polyoxyethylene hydrogenated castor oil ("HCO-60", trade name; product by Nikko Chemicals) or "PLURONIC F68" (polyoxyethylene-polyoxypropylene copolymerized substance; produced by Asahi Denka Kogyo K. K.); antioxidant such as sodium sulfite or sodium ascorbate; lubricant such as magnesium stearate, calcium stearate, talc, sucrose fatty acid ester, polyethylene glycol or stearic acid; sour agent such as citric acid, tartaric acid or malic acid; artificial sweetener such as sodium saccharin, dipotassium glycyrrhizinate, aspartame, stevia or somatin; flavor such as lemon, lemon lime, orange or menthol; colorant such as Food Yellow 5, Food Red 2 or Food Blue 2; and stabilizer.

In order to suppress the taste, the solid dispersion in the tablet or granule preparation, or the tablet or granule preapration itself may be coated in a known manner. Examples of the coating agent include hydroxypropylcellulose, ethylcellulose, hydroxymethylcellulose and hydroxypropylcellulose. They may be used either singly or in combination and coating of a single layer or two or more layers is possible. The coating is carried out in a known manner, for example, by the pan coating method, fluidized bed coating method or tumbling coating method through spraying a dispersion or solution of a coating base in water or an organic solvent.

BEST MODE FOR CARRYING OUT THE INVENTION

Hereinafter, the present invention will be specifically described with reference to Examples. It should however be understood that the scope of the present invention is not limited to or by Examples. Incidentally, preparations obtained in Examples and Comparative Examples were evaluated according to the disintegration property test was evaluated by the dissolution test or disintegration test.

[Dissolution Test]

With respect to the tablets prepared in Examples 1 to 5 and Comparative Examples 1 to 3, a test was performed at 100 r.p.m. in 500 ml of a first fluid (pH: 1.2) as specified in the disintegration test method of *Japanese Pharmacopoeia* by employing the second method (paddle method) of the dissolution test method of *Japanese Pharmacopoeia*, 13th Edition and a time required for dissolution of 75% of the medicament was measured.

[Disintegration Test]

With respect to the tablets obtained in Examples 6 to 8, a test was performed in accordance with the disintegration test method of *Japanese Pharmacopoeia*, 13th Edition using water as the test solution.

(Preparation of a Solid Dispersion of Compound A1)

In 45.5 parts by weight of a 9:1 by weight mixed solution of methanol and water, 1 part by weight of Compound A1, 3 parts by weight of "HPMC 2910" and 0.5 parts by weight of "Polysorbate 80" were dissolved, and a solid dispersion was prepared by spray drying.

EXAMPLE 1

45 mg of the solid dispersion obtained above (preparation of a solid dispersion of Compound A1), 75 mg of lactose and 30 mg of sodium bicarbonate were uniformly mixed. The resulting mixture was formed into tablets each having a weight of 150 mg (Compound A1; 10 mg) and a diameter of 7.5 mm by an oil press at a tabletting pressure of 500 kg/punch. The result of the dissolution test was 4 minutes.

EXAMPLE 2

45 mg of the solid dispersion obtained above (preparation of a solid dispersion of Compound A1), 90 mg of lactose and 15 mg of sodium bicarbonate were uniformly mixed. The resulting mixture was formed into tablets each having a weight of 150 mg (Compound A1; 10 mg) and a diameter of 7.5 mm by an oil press at a tabletting pressure of 500 kg/punch. The result of the dissolution test was 5 minutes.

EXAMPLE 3

45 mg of the solid dispersion obtained above (preparation of a solid dispersion of Compound A1), 75 mg of lactose and 30 mg of potassium bicarbonate were uniformly mixed. The resulting mixture was formed into tablets each having a weight of 150 mg (Compound A1; 10 mg) and a diameter of 7.5 mm by an oil press at a tabletting pressure of 500 kg/punch. The result of the dissolution test was 5 minutes.

EXAMPLE 4

In 4,550 g of a 9:1 by weight mixed solution of methanol and water, 100 g of Compound A1, 300 g of "HPMC 2910" and 50 g of "Polysorbate 80" were dissolved. Then, by using a fluidized bed granulator ("Uniglatt", manufactured by Okawara Seisakujo), 442 g of lactose and 150 g of sodium bicarbonate were fluidized and the solution prepared above was sprayed to the fluidized mixture, whereby granulated powder was obtained. Then, 834 g of the resulting granulated powder, 240 g of crystalline cellulose ("Avicel PH102", trade name; produced by Asahi Kasei), 120 g of croscarmellose sodium ("Ac-Di-Sol", trade name; produced by Asahi Kasei) and 6 g of magnesium stearate were uniformly mixed. The resulting mixture was formed into tablets each having a weight of 150 mg (Compound A1; 10 mg) and a diameter of 7.5 mm by a rotary tabletting machine (manufactured by Hata Seisakujo) at a tabletting pressure of 700 kg/punch. The result of the dissolution test was 9 minutes.

EXAMPLE 5

In 4,550 g of a 9:1 by weight mixed solution of methanol and water, 100 g of Compound A1, 300 g of "HPMC 2910"

and 50 g of polyethylene hydrogenated castor oil (60) ("Nikkol 60", trade name; produced by Nikko Chemicals) were dissolved. Then, by using a fluidized bed granulator ("Uniglatt", manufactured by Okawara Seisakujo), 435 g of lactose and 150 g of sodium bicarbonate were fluidized and the solution obtained above was sprayed to the fluidized mixture, whereby granulated powder was prepared. Then, 828 g of the resulting granulated powder and 1572 g of lactose were mixed uniformly, and the resulting mixture was filled into capsules (No. 1 capsule) each in an amount of 0.3 g (Compound A1; 10 mg) per capsule, whereby preparing capsules. The result of the dissolution test was about 4 minutes.

COMPARATIVE EXAMPLE 1

45 mg of the solid dispersion obtained above (in the preparation of a solid dispersion of Compound A1), 75 mg of lactose and 30 mg of croscarmelllose sodium ("Ac-Disol", trade name; produced by Asahi Kasei) were uniformly mixed. The resulting mixture was formed into tablets each having a weight of 150 mg (Compound A1; 10 mg) and a diameter of 7.5 mm by an oil press at a tabletting pressure of 500 kg/punch. The result of the dissolution test was 48 minutes.

COMPARATIVE EXAMPLE 2

45 mg of the solid dispersion obtained above (in the preparation of a solid dispersion of Compound A1), 75 mg of lactose and 30 mg of carboxymethyl starch sodium ("Primojel", trade name; produced by Matsutani Chemical) were uniformly mixed. The resulting mixture was formed into tablets each having a weight of 150 mg (Compound A1; 10 mg) and a diameter of 7.5 mm by an oil press at a tabletting pressure of 500 kg/punch. The result of the dissolution test was 27 minutes.

COMPARATIVE EXAMPLE 3

45 mg of the solid dispersion obtained above (in the preparation of a solid dispersion of Compound A1), 75 mg of lactose and 30 mg of sodium carbonate were uniformly mixed. The resulting mixture was formed into tablets each having a weight of 150 mg (Compound A1; 10 mg) and a diameter of 7.5 mm by an oil press at a tabletting pressure of 500 kg/punch. The result of the dissolution test was 55 minutes.

(Results of Dissolution Test)

Preparations of the present invention which had been obtained in Examples 1 to 5 were subjected to the dissolution test, each resulting in the dissolution time within 9 minutes. On the other hand, preparations obtained in Comparative Examples 1 to 3 were subjected to a dissolution test, each resulting in the dissolution time of 27 minutes or longer (cf. Table 1).

The disintegrant which was ordinarily used and the salt substance which comprises an alkali and a weak or strong acid and having not an endothermic standard enthalpy of solution, that is, having an exothermic standard enthalpy of solution like sodium carbonate (−26.7 kJ/mol) which was used as an effervescence tablet did not attain rapid disintegration. On the other hand, it was confirmed that the preparations according to the present invention each exhibited a rapidly disintegrable property.

TABLE 1

|  | Examples | | | | | Comparative Examples | | |
|---|---|---|---|---|---|---|---|---|
|  | 1 | 2 | 3 | 4 | 5 | 1 | 2 | 3 |
| Dissolution test (min) | 4 | 5 | 5 | 9 | 4 | 48 | 27 | 55 |

(Preparation of a Solid Dispersion of Compound B)

In methanol, 1 g of Compound B, 3.5 g of "HPMC 2910" and 0.5 g of polyoxyethylene hydrogenated castor oil ("HCO-60", trade name; produced by Nikko Chemicals) were dissolved, and a solid dispersion was prepared by spray drying.

EXAMPLE 6

Then, 100 mg of the the solid dispersion obtained above (preparation of a solid dispersion of Compound B) and 50 mg of sodium bicarbonate were mixed uniformly. The resulting mixture was formed into tablets each having a weight of 150 mg and a diameter of 7.5 mm by an oil press at a tabletting pressure of 500 kg/punch. The result of the disintegration test was 10 minutes.

EXAMPLE 7

A 200 mg portion of the solid dispersion obtained above (in the preparation of a solid dispersion of Compound B) and 75 mg of sodium bicarbonate were uniformly mixed, and the resulting mixture was formed into tablets each having a weight of 275 mg and a diameter of 7.5 mm by an oil press under a tabletting pressure of 500 kg/punch. The result of the dissolution test was 15 minutes.

EXAMPLE 8

A 200 mg portion of the solid dispersion obtained above (in the preparation of a solid dispersion of Compound B) and 100 mg of sodium bicarbonate were uniformly mixed, and the resulting mixture was formed into tablets each having a weight of 300 mg and a diameter of 7.5 mm by an oil press under a tabletting pressure of 500 kg/punch. The result of the dissolution test was 10 minutes.

(Results of Dissolution Test)

Results of the dissolution test carried out on the tablets obtained in Examples 6 to 8 were all within 15 minutes.

In consequence, the pharmaceutical composition of the present invention exhibits rapid disintegration of sparingly soluble medicaments having completely different structures regardless of the presence or absence of their salts and is a medicament preparation technique having high general-purpose performance.

INDUSTRIAL APPLICABILITY

The pharmaceutical composition according to the present invention exhibits rapid disintegration. Owing to rapid dissolution of a sparingly soluble medicament from the composition, good bioavailability can be attained. In addition, the preparation comprising the above pharmaceutical composition therefore exhibits rapid disintegration independently of the pH in the digestive tract and the medicament contained in the preparation exhibits rapid dissolution.

The invention of claimed is:

1. A pharmaceutical composition comprising:
a poorly water soluble drug having a drug solubility of 100 ml or more as a volume of solvent required for dissolving 1 g;
a gel-forming water-soluble polymer; and
a salt substance consisting of an alkali and a weak or strong acid and said salt substance having an endothermic standard enthalpy of solution (KJ/mol) or heat of solution (Kcal/mol) wherein said salt substance is selected from the group consisting of sodium bicarbonate, potassium bicarbonate, potassium sulfate, potassium chloride, sodium chloride and potassium dihydrogenphosphate; a surfactant in the range of 0.1 to 3 parts by weight based on 1 part by weight of the poorly water soluble drug;
wherein said poorly water soluble drug is held in said gel forming water soluble polymer as a solid dispersion
wherein said drug, said gel-forming water-soluble polymer and said salt substance are added in amounts (wt./wt %) of 1 to 30%, 3 to 60%, and 3 to 50%, respectively based on the total amount of the preparation, and
without adding any organic acid, and
wherein the poorly water soluble drug is 4'-[(2-methyl-1,4,5,6-tetrahydroimidazol[4,5-d][1]benzoazepin-6-yl)carbonyl]-2 phenylbenzanilide or a salt thereof.

2. A pharmaceutical composition comprising:
a poorly water soluble drug having a drug solubility of 100 ml or more as a volume of solvent required for dissolving 1 g;
a gel-forming water-soluble polymer; and
a salt substance consisting of an alkali and a weak or strong acid and said salt substance having an endothermic standard enthalpy of solution (KJ/mol) or heat of solution (Kcal/mol) wherein said salt substance is selected from the group consisting of sodium bicarbonate, potassium bicarbonate, potassium sulfate, potassium chloride, sodium chloride and potassium dihydrogenphosphate; a surfactant in the range of 0.1 to 3 parts by weight based on 1 part by weight of the poorly water soluble drug; a surfactant
wherein said poorly water soluble drug is held in said gel forming water soluble polymer as a solid dispersion
wherein said drug, said gel-forming water-soluble polymer and said salt substance are added in amounts (wt./wt %) of 1 to 30%, 3 to 60%, and 3 to 50%, respectively based on the total amount of the preparation, and
without adding any organic acid, which comprises a medicament of 4'-[(2-methyl- 1,4,5,6-tetrahydroimidazo[4,5-d][1]benzoazepin-6-yl)carbonyl]-2 phenylbenzanilide or a salt thereof and a pharmaceutical carrier, said preparation exhibiting a dissolution of 75% of said medicament within 15 minutes when a test is performed using 500 ml of a first fluid (pH 1.2) at 100 r.p.m. in accordance with a second method (paddle method) for dissolution as specified in Japanese Pharmacopoeia, 13th Edition.

3. The pharmaceutical preparation according to claim 2, wherein the pharmaceutical carrier comprises a gel-forming water-soluble polymer, and a salt substance comprising an alkali and a weak or strong acid, and said salt substance having an endothermic standard enthalpy of solution or heat of solution.

* * * * *